(12) United States Patent
Bell

(10) Patent No.: US 8,642,324 B2
(45) Date of Patent: Feb. 4, 2014

(54) CONTINUOUS FLOW WORM FARM

(75) Inventor: Benjamin Bell, Auckland (NZ)

(73) Assignee: LOW Impact Limited, Onehunga, Auckland (NZ)

( * ) Notice: Subject to any disclaimer, the term of this patent is extended or adjusted under 35 U.S.C. 154(b) by 0 days.

(21) Appl. No.: 13/146,441

(22) PCT Filed: Feb. 4, 2010

(86) PCT No.: PCT/NZ2010/000016
§ 371 (c)(1),
(2), (4) Date: Jul. 27, 2011

(87) PCT Pub. No.: WO2010/090537
PCT Pub. Date: Aug. 12, 2010

(65) Prior Publication Data
US 2011/0281345 A1 Nov. 17, 2011

(30) Foreign Application Priority Data

Feb. 5, 2009 (NZ) .......................................... 574676
Dec. 1, 2009 (AU) .................................. 2009905863

(51) Int. Cl.
*C12M 1/00* (2006.01)
*C05F 17/02* (2006.01)
(52) U.S. Cl.
CPC ................................. *C05F 17/0205* (2013.01)
USPC ........................................ 435/290.1; 119/6.7
(58) Field of Classification Search
CPC .................................................. C05F 17/0205
USPC ..................................... 435/290.1–4; 119/6.7
See application file for complete search history.

(56) References Cited

U.S. PATENT DOCUMENTS

| | | | | |
|---|---|---|---|---|
| 4,105,412 | A | * | 8/1978 | Petzinger ....................... 422/275 |
| 5,031,796 | A | * | 7/1991 | Schafer et al. ................ 220/571 |
| 7,883,885 | B2 | * | 2/2011 | Schmidl ..................... 435/290.1 |
| 2002/0081717 | A1 | * | 6/2002 | Morrison ................... 435/290.1 |
| 2008/0213876 | A1 | * | 9/2008 | Morrison ................... 435/290.1 |

FOREIGN PATENT DOCUMENTS

| | | | |
|---|---|---|---|
| AU | 737050 | B2 | 2/1998 |
| AU | 712227 | B2 | 12/1998 |
| EP | 0091495 | A1 | 10/1983 |
| JP | 10-114590 | A | 5/1998 |
| WO | 87/00003 | A1 | 1/1987 |
| WO | 99/62844 | A1 | 12/1999 |
| WO | 00/53543 | A1 | 9/2000 |

OTHER PUBLICATIONS

Translation of JP 10114590A, May 1998 (reference provided by applicant).*

* cited by examiner

*Primary Examiner* — Michael Hobbs
*Assistant Examiner* — Liban Hassan
(74) *Attorney, Agent, or Firm* — Richard M. Goldberg

(57) ABSTRACT

An apparatus for the treatment of organic matter with worms, includes a receptacle with a side wall at least a portion of which is downwardly tapering to facilitate compression of organic matter as organic matter is processed, an upper entry aperture for loading the receptacle with the organic matter and worms, a lower discharge aperture for discharging compressed material including castings and organic matter, and a base lid adapted to releasably close the discharge aperture and to permit removal of the compressed material from the receptacle.

11 Claims, 5 Drawing Sheets

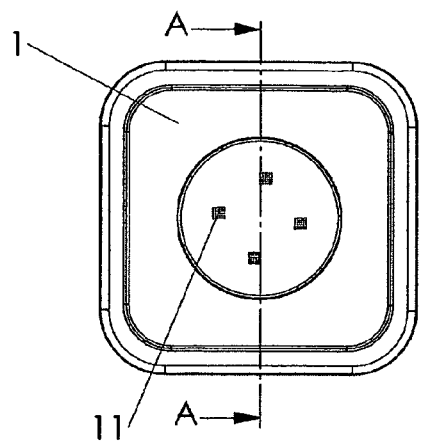
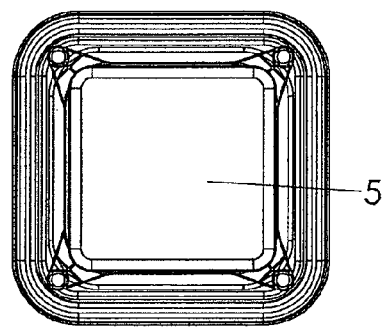
Fig. 2.    Fig. 3.
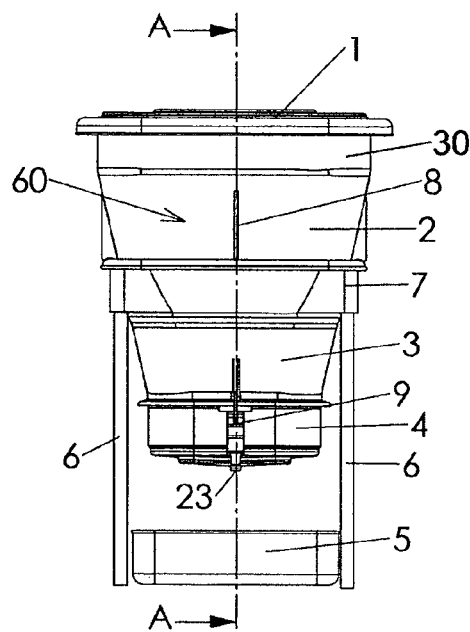
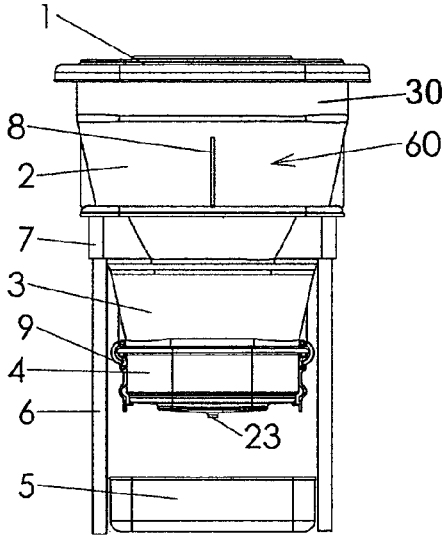
Fig. 4.    Fig. 5.

CONTINUOUS FLOW WORM FARM

CROSS-REFERENCE TO RELATED APPLICATIONS

The present application claims priority from New Zealand Provisional Patent Application No 574676 filed on 5 Feb. 2009 and Australian Provisional Patent Application No 2009905863, the contents of which are incorporated herein by reference.

TECHNICAL FIELD

This invention relates to an apparatus for the treatment of organic waste and particularly, but not exclusively, to an apparatus for the composting of domestic organic waste. The present invention also relates to an apparatus for the breeding and supply of compost worms.

BACKGROUND ART

As awareness of the environmental cost, and the economic cost for the disposal of organic waste has increased, individuals, companies and government authorities have a desire to use methods other than landfill when disposing of organic waste. In some countries, minimisation of organic waste to landfill is required by law.

Domestic waste in particular has a high proportion of food waste, which when processed correctly, yields both high quality liquid and solid fertiliser.

In this context, vermiculture (worm farming) has proven to be a successful means of treating organic waste streams. Generally, the worm farm comprises a container containing soil, organic matter and compost worms. Three of the most common species of worms used in vermiculture are *Eisenia Foetida, Lumbricus Rubellus* and *Perionyx Excavatus*. Organic waste is digested by the worms and ejected as castings. The castings and remaining organic matter contain high levels of nutrients and are suitable for use as fertiliser.

Conventional worm farms are generally of two types, tiered systems and continuous flow systems.

Tiered systems, such as Australian patent 737050, comprise two or more stackable trays, the lowermost a solid base with a drainage system to remove excess moisture. Additional trays are added as required and have a perforated base to allow the passage of both worms and liquids. The trays may have slightly sloping sides with the result the floor of a tray rests directly upon the organic waste contained in the tray immediately below. The trays are periodically rotated in order to remove processed waste from the lowermost tray.

Continuous flow systems, such as Australian patent 712227, comprise a single container, either elevated from the ground, or resting directly upon it. Organic waste is introduced to the top of the container and digested by the worm population within. The processed organic matter passes through container to the floor where it generally exits via a wide aperture mesh and falls onto a tray. Excess liquid is then drained from the finished castings. In some systems, the walls of the container may also be formed of a wide aperture mesh, allowing castings, liquid and worms to pass through and fall to the collection tray below.

Both systems have significant disadvantages. Tiered systems result in separate populations of worms either becoming stranded in individual trays due to a gap arising between the top of the waste present in the tray and the bottom of the tray immediately above it, or the worms failing to migrate from the lower trays to the organic waste present in higher trays because sufficient nutrients are available in the tray they are inhabiting. Worms are also able to migrate downwards to the lowest tray and drown in any liquid present. Further, due to the fact that trays must be periodically rotated, the lifecycle of the worms is disturbed. Still further, the trays when full of organic waste are a considerable weight for a single individual to lift. To overcome this problem a shallow tray may be used to enable an operator to lift its weight. However the shallow tray prevents the finished castings within from becoming compressed, allowing worms to remain active in the castings and increasing the handling weight of finished castings. In addition, trays must be entirely emptied to access the older castings situated in the bottom of the tray, and the lower tray may have substantial numbers of adult worms present which must be separated from the castings prior to use.

As stated, continuous flow systems generally rely on a wide aperture mesh to prevent the organic waste present from falling through the farm. As castings pass through the mesh and fall to a collection tray they have high moisture content and are uncompressed. The mesh in a continuous flow design can become blocked by unprocessed vegetable fibre or with the inadvertent introduction of foreign material such as plastic coated paper. Large numbers of worms and worm eggs can be present in the castings, and are unable to re-enter the farm subsequent to falling into the collection tray, reducing the overall capacity of the farm to process waste. Continuous flow designs with doors in the lower part of the farm for removal of processed waste allow removal of waste only from the side of the container in which the door is located. This results in the uneven removal of castings from within the farm.

Unless the context clearly requires otherwise, through out the description and the claims, the words 'comprise' and 'comprising', and the like are to be construed in an inclusive as opposed to an exclusive or exhaustive sense; that is to say in the sense of "including, but not limited to".

SUMMARY OF THE INVENTION

The present invention concerns an apparatus for the treatment of organic matter with worms. The apparatus comprises a receptacle with a side wall at least a portion of which is downwardly tapering to facilitate compression of organic matter as said organic matter is processed, an upper entry aperture for loading said receptacle with said organic matter and worms and a lower discharge aperture for discharging compressed material comprising castings and organic matter. The apparatus further comprises a base lid adapted to releasably close said discharge aperture and to permit removal of said compressed material from said receptacle.

Preferably the receptacle has a central axis. The downwardly tapering side wall may be angled at between 5 and 20 degrees with respect to the central axis. More preferably, the downwardly tapering side wall is angled at between 10 and 15 degrees with respect to the central axis. More preferably the downwardly tapering side wall is angled at about 12 degrees. Said portion of the receptacle may have a trapezoid shaped cross section in elevation.

Preferably the receptacle has a square, circular, elliptical or rectangular cross section in plan view from the top.

The base lid may be in the form of a second receptacle having side walls to retain said compressed material after disengagement of said base lid from said receptacle. In one embodiment the base Hd or second receptacle is adapted to pivotably engage the receptacle. Optionally, the base lid or second receptacle removeably engages the receptacle.

In an embodiment a lower periphery of said side wall is non-tapered. The base lid may comprise a sleeve adapted to fit said lower periphery and to retain the compressed material after disengagement of said base lid from said receptacle. The lower periphery of said side wall may have a substantially square or rectangular shaped cross section in elevation. The lower periphery of said side wall may have a circular, elliptical, square or rectangular shaped cross section in plan view.

In an embodiment a height of said lower periphery is substantially equal to a height of said sleeve of said base lid. As will be appreciated, in such an embodiment the volume of the area occupying the lower periphery of the receptacle may be substantially that of the volume occupying the base lid.

In an embodiment an upper periphery of said side wall may be non-tapered. The upper periphery of said side wall may have a circular, elliptical, square or a rectangular shaped cross section in plan view.

In an embodiment an interior surface of the receptacle may be smooth to enhance the rate at which said organic matter is compressed as said organic matter is processed.

In an embodiment the base lid/second receptacle comprises a filter and a drain assembly which are adapted to enable the passage of liquid there-through and restrict the passage of compressed material. The filter and the drain assembly may be provided for in a floor of the base lid/second receptacle.

In an embodiment the apparatus may further comprise a support for elevating said receptacle off the ground.

In an embodiment the apparatus may further comprise an entry lid adapted to engage said receptacle and releasably close said upper entry aperture. The entry lid may comprise perforations adapted to allow the passage of gasses and liquids and to substantially prevent the entry of insects, or exit of worms. The entry lid of the receptacle may be further adapted such that when the lid is inverted it is releasably engageable to a top of the receptacle to facilitate drying of organic matter harvested from the receptacle.

Preferably the material is manufactured from a high density polyethylene or similar plastics or plasticized materials having a sufficient degree of rigidity. Optionally the receptacle may be formed from a non corroding metal or a lightweight non porous sheet material.

It is preferred that the passage of liquid is unrestricted from the receptacle. The drained liquid can be collected in a suitable receptacle placed immediately below the receptacle. This liquid collecting receptacle may be in direct or indirect communication with the base lid.

BRIEF DESCRIPTION OF THE DRAWINGS

Features and advantages of the present invention will become apparent from the following description of an embodiment, by way of example only, with reference to the accompanying drawings, wherein like numerals refer to like parts throughout, and in which:

FIG. 2 is a top view of the apparatus as shown in FIG. 1;

FIG. 3 is a bottom view of the apparatus as shown in FIG. 1;

FIG. 4 is a front elevation of the apparatus as shown in FIG. 1;

FIG. 5 is a side elevation of the apparatus as shown in FIG. 1;

FIG. 11.A illustrates a detailed view of the top of an upper periphery shown in FIG. 11;

FIG. 11.B illustrates a clip arrangement as shown in FIG. 11; and

DETAILED DESCRIPTION OF THE DRAWINGS

Figure 1:
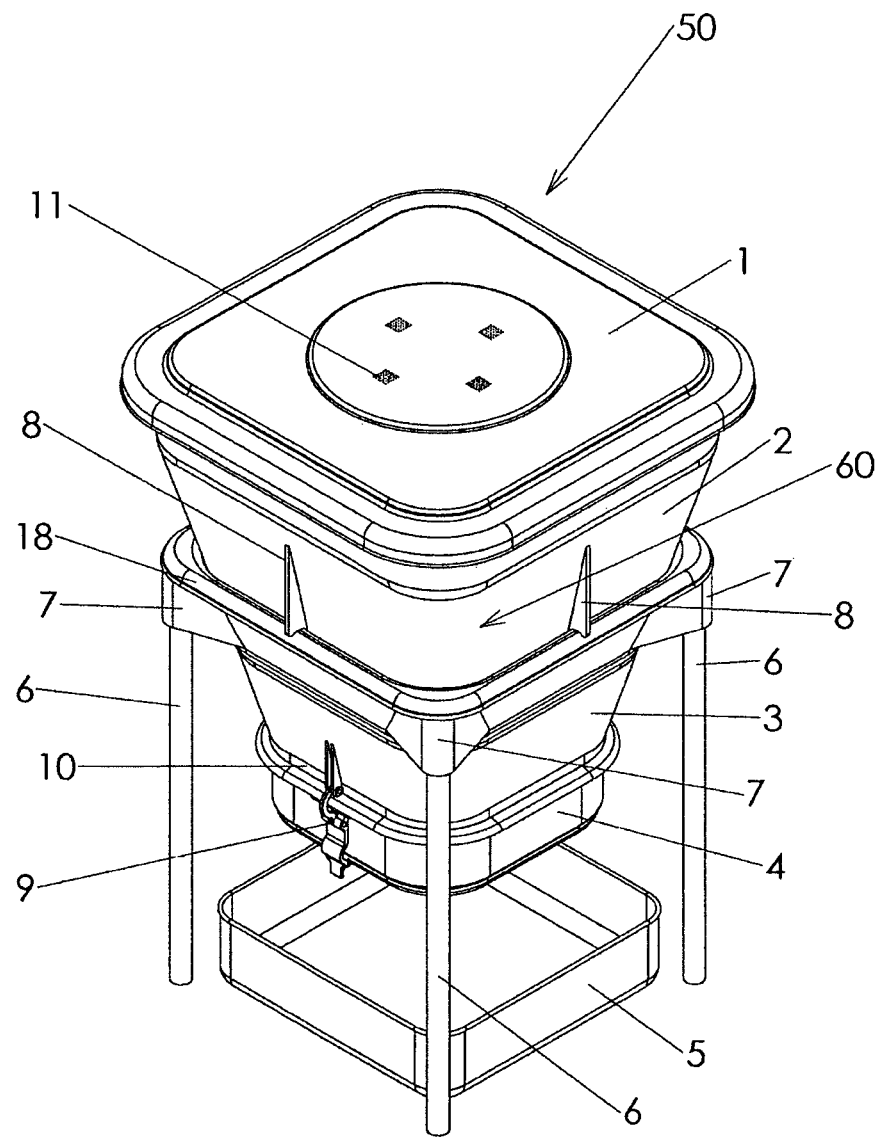
FIG. 1 is a perspective view of an apparatus for the treatment of organic matter with worms.

FIGS. 1 to 12 illustrate an apparatus 50 for the treatment of organic matter with worms. The apparatus 50 comprises a receptacle 60 which is formed of two separate parts, an upper body 2 and a lower body 3. The receptacle also includes an upper periphery 30 and a lower periphery 40 which are integrally formed with the upper body 2 and a lower body respectively. The apparatus 50 further includes a base lid in the form of a detachable outlet cover 4.

The apparatus further includes an entry lid 1 which is adapted to engage the upper periphery 30 of the receptacle 60 and releasably close the receptacle's upper entry aperture. The entry lid 1 is modified with a plurality of holes 11 of sufficient size to allow the passage of gasses and liquids but prevent the access of undesirable insects and/or the exit of worms. The upper entry aperture is covered during operation with the entry lid 1.

The receptacle 60 and base lid 1 are formed from a high density polyethylene. In normal operation the upper body 2 fits into the lower body 3, and is located in place by both an interference fit 19 with the lower body 3, and a plurality of fillets 8 each projecting perpendicular to the outer face of said upper body walls.

The receptacle 60 is raised from the ground to a convenient operating height by a support. The support includes a frame 18 which supports four vertical legs 6, each of tubular nature. Each leg 6 is located in a respective socket 7 of the frame 18 and a socket is located in each of the four upper corners of said lower body. When the receptacle 60 is lowered through the frame 18 the fillets 8 projecting perpendicular from the outer face of the walls of the upper body 12 rest on the frame 18.

As more clearly seen with reference to FIGS. 4 and 5, the receptacle 60 has four side walls, at least a portion of each of which is downwardly tapering. The receptacle 60 has a central axis (designated by the line A-A shown in FIG. 4). The tapering of the side wall is angled at about 12.5 degrees with respect to the central axis. As is evident in this embodiment, this portion of the side walls has a trapezoid shaped cross section in elevation. Each of the upper periphery 30 and the lower periphery 40, have a rectangular shaped cross section in elevation and a square cross section in plan view (see FIG. 8). A width of the top of the trapezoid shaped cross section in elevation is greater than a width of the bottom of the trapezoid shaped cross section in elevation to facilitate the rate at which organic matter is compressed as it is processed. Hence the upper entry aperture 60 is larger than the lower discharge aperture of the receptacle 60.

The interior surface of the receptacle 60 is smooth or polished to facilitate the unrestricted movement of processed organic matter downwards through the receptacle 60. The radius on the wall edges is also conducive to the unrestricted passage of organic material.

Figure 6:
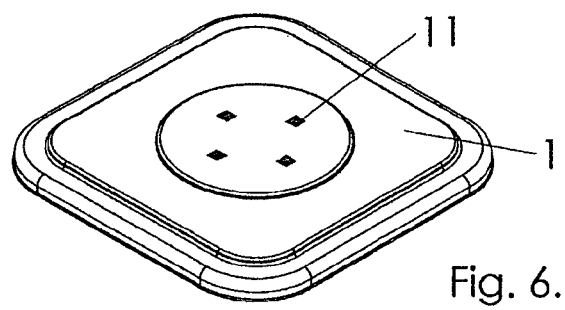
FIG. 6 is a perspective view of an entry lid of the apparatus as shown in FIG. 1.
Figure 7:
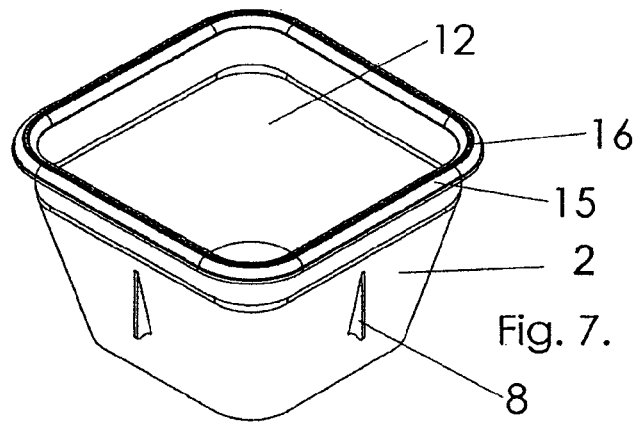
FIG. 7 is a perspective view of an upper portion of the receptacle as shown in FIG. 1.
Figure 8:
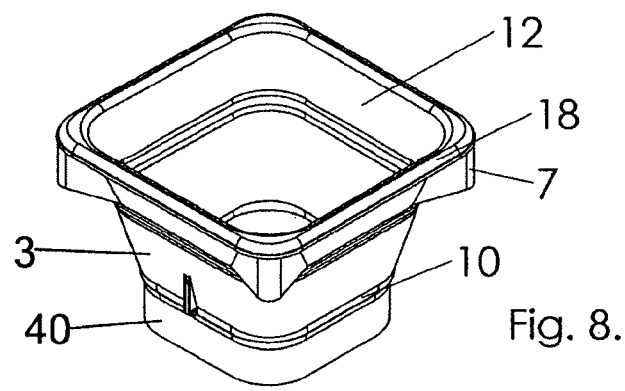
FIG. 8 is a perspective view of a lower portion of the receptacle as shown in FIG. 1.

Referring to FIGS. 6 and 7, the upper periphery 30 has a rolled edge 15 around the circumference to effect dimensional stability to the receptacle 60. An upper surface of said rolled edge 15 includes a raised lip 16 projected around the circumference of the receptacle 60, which creates an interference fit with two similar lips 17 located on a lower surface of the entry lid, to provide a seal preventing the access of insects to, and the exit of worms from the receptacle 60 when the lid 1 is positioned in place.

Figure 11:
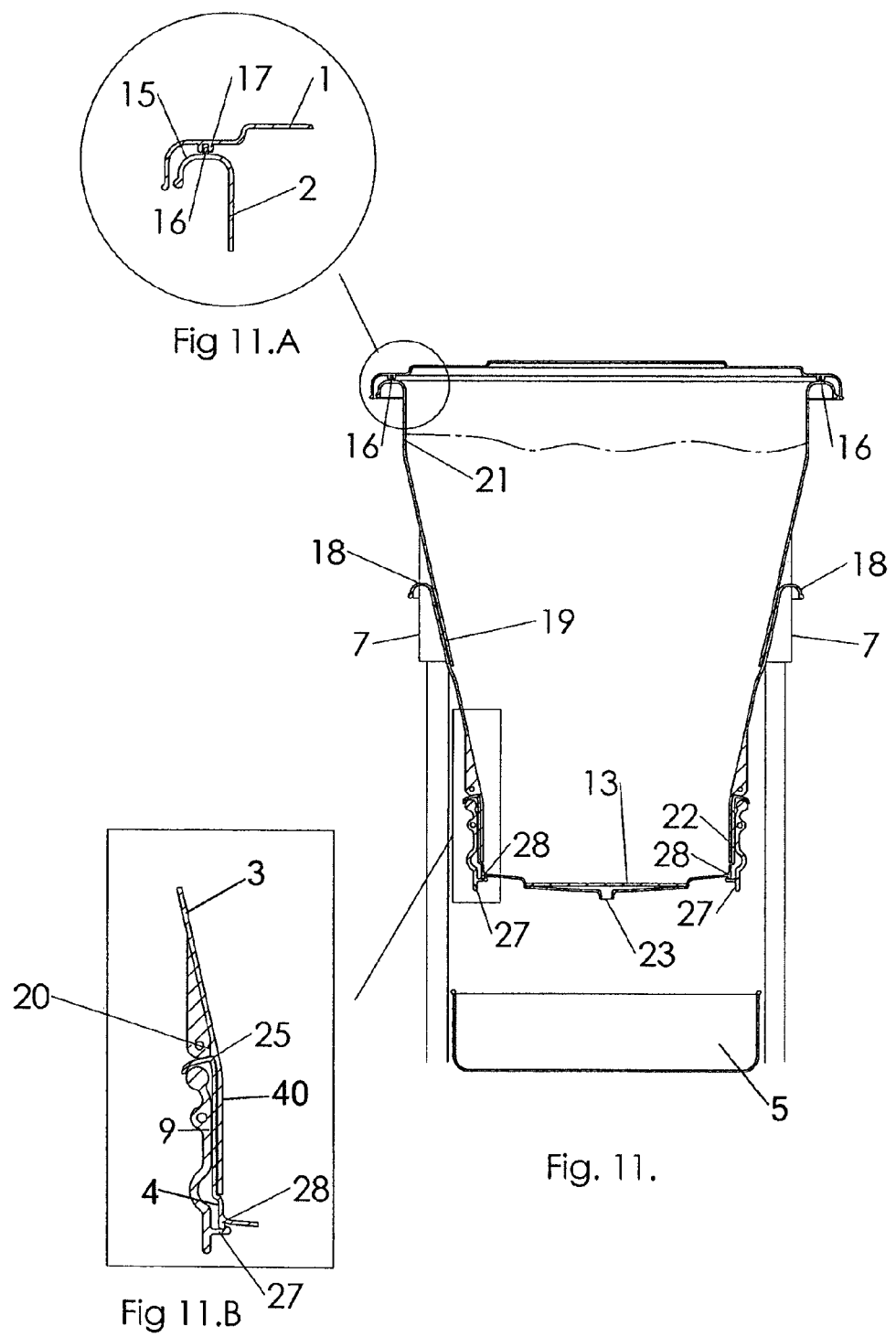
FIG. 11 is a cross sectional view through A-A of FIGS. 2 & 4.
Figure 12:
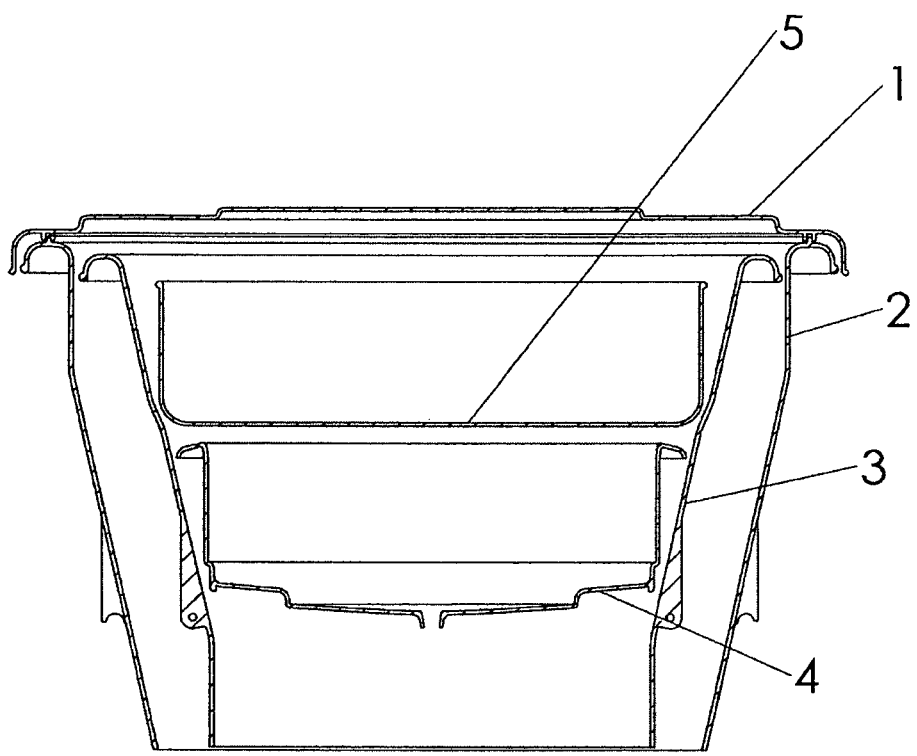
FIG. 12 is a cross section of an embodiment of the apparatus when packed for sale or freight.

The outlet cover 4 encloses the lower periphery 40 of the lower body 3 of the receptacle 60. The outlet cover 4 has four vertical walls with a radius where the edges meet at both the edges and bottom face. With reference to FIGS. 11 and 11B, said outlet cover 4 forms an interference fit 25 with a rim 20 located on the outer face of the walls of the lower body 3, the interference fit having the effect of restricting the passage of liquids and/or insects there-through when the outlet cover is fixed in place.

In operation the outlet cover 4 is secured over the exit of the lower periphery 40 of lower body 3 and held in place with a clip arrangement 9 on two of the receptacles four sides. The clips are of an over-centre type and hold the outlet cover 4 firmly against said rim when closed. The clips are prevented from opening accidentally when closed, by a lock catch 27 adapted for the purpose, situated on the body of the clip, which locates into a corresponding tab 28 located on the outer edge of the outlet cover walls. The clip is unlocked by the application of pressure to the lower part of the clip.

Figure 9:
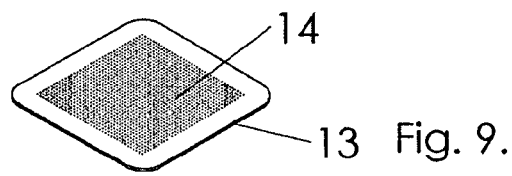
FIG. 9 is a perspective view of a filter of the apparatus as shown in FIG. 1.
Figure 10:
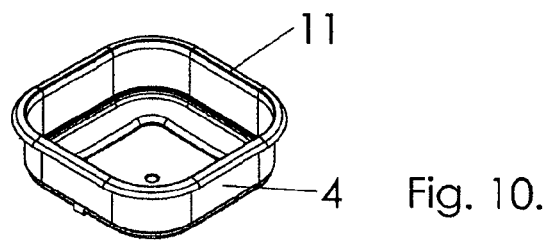
FIG. 10 is a perspective view of a base lid of the apparatus as shown in FIG. 1.

Referring to FIGS. 9 and 10, a floor of the outlet cover 4 is modified to hold a filter 13 in place, with apertures of sufficient size 14 to allow liquids to pass there-through but substantially restricting the passage of compressed material. A drain hole 23 in the base of the outlet cover 4 allows any liquid passing through the filter to freely drain from the receptacle 60 to a suitable receptacle 5 placed below.

When the clips are released, the outlet cover 4 slides downwards away from the lower periphery 40 of the lower body 3, allowing the removal of material previously withheld from exiting the receptacle 60 by the outlet cover 4 and filter arrangement.

In operation, the receptacle 60 is filled or partially filled with soil and/or organic material with an initial population of worms.

Organic waste is placed on the surface of the organic material within the receptacle 60, and subsequently processed by the compost worm population therein. Compost worms are surface feeders. They are adapted to live in the humus layer on the forest floor and do not make burrows as do common earthworms. The worms are most active in the upper 300 mm of the container 60 where the organic material is fresh, aerated and un-compacted. The majority of the worm population within the receptacle will generally be found within the top 250 mm of the surface. The design has the additional advantage of maximising the available surface area in the upper periphery 30 of the receptacle in order to optimise the productivity of the worms within it, while simultaneously reducing the surface area of the lower periphery 40 to facilitate the easy removal of castings.

As a result of the compression the castings undergo as they move through the farm, caused by the weight of fresh castings accumulating, the compost worms are naturally forced toward the surface of the receptacle. If the receptacle 60 has sufficient depth for this process to take place, the castings in the lower part of the receptacle will be largely free of worms. Typically this will require a depth of castings greater than 350 mm.

It is preferable that the waste is introduced to the farm at a rate equal to the ability of the worms within to consume it. This prevents uneaten waste rotting within the farm causing undesirable anaerobic conditions.

Worms have a gizzard much like that found in birds, which in combination with their mouth parts reduce the organic matter they consume and subsequently excrete to a very fine and uniform consistency. The liquid draining from a properly functioning worm farm will have a high proportion of suspended solids, the majority of which will be matter finely divided by its passage through digestive system of the worms within the farm. This result reduces the frequency with which, and the volume of, organic matter removed from the receptacle 60.

In dry conditions, and dependent on the organic matter introduced to the receptacle 60, water may have to be periodically introduced to the receptacle 60 to maintain optimum growing conditions for the worms. In some instances additional organic material or lime may need to be introduced in order to balance the acidity of the organic material introduced to meet an ideal PH of between 6.5-7.5.

Over a period of time the worms increase in population, along with the amount of processed waste captured by the receptacle 60.

As organic material passes down through the receptacle 60, the slope of the side walls, and the weight of fresh organic material above, cause the organic material to become compressed as it is prevented from passing from the receptacle 60 by the outlet cover 4, and therefore forced into a smaller volume, with the benefit of both forcing liquid to drain from the organic material and castings, via the filter 13 and drain 23, and encouraging any worms present to migrate upwards to the active surface layer.

Advantageously liquid is allowed to pass freely from the receptacle 60, whilst compressed material comprising castings and organic material are prevented from exiting the receptacle 60 by the outlet cover 4, filter 13 and drain arrangement 23. Should any worms be present in the compressed material they are discouraged from exiting the receptacle 60 by the outlet cover 4, filter 13 and drain arrangement 23.

An unexpected result of the design, and a benefit to its function, is that liquid forced from the organic material by the weight of subsequent organic material placed in the receptacle 60 above it, first migrates to the outside edges of the organic matter within the receptacle 60, where-upon it then travels downwards adjacent to the interior surface of the wall of the receptacle 60 and the organic material within. The liquid forms a lubrication layer between the wall of the receptacle 60 and the organic material, reducing the resistance against the interior walls and therefore assisting the passage downwards of organic material within the receptacle 60.

The angle with which the sidewalls converge is important to the design of the apparatus. Walls of lower converging angles reduce the compression undergone by the organic material as it is pushed through the receptacle 60. In contrast, walls of higher converging angles prevent the organic material from passing evenly through the receptacle 60, as the pressure on the organic waste at the edges of the receptacle 60 is less than that at the centre, resulting in organic material close to the edges of the receptacle 60 failing to exit the receptacle 60 when the outlet lid 4 is removed. Because the castings ejected by worms are of a very uniform consistency, the results of the compression caused by the sloping walls 12 can be easily and reliably controlled.

Extensive experimentation with various configurations of the degree of the downward taper of the respective portion of the receptacle's sidewalls has determined that the ideal angle of sidewall convergence, for the processing of organic food waste typical of that produced by a household or commercial kitchen, and using commonly available compost worms, is substantially 12.5 (twelve point five) degrees from the vertical plus or minus 0.5 (zero point five) of a degree. Angles greater than 20 (twenty) degrees and less than 5 (five) degrees from the vertical have significant disadvantages to the functioning of the apparatus. The optimum total depth of the trapezoid section of the receptacle is found to be greater than 350 mm, to allow egg casings present in the receptacle to have hatched before castings are removed, and the finished castings sufficient time to cure.

The accompanying drawings (although not to scale) illustrate what is considered to be the optimum proportions for a design of this type, used for the purpose of processing organic waste typical of that produced by a household or commercial kitchen, and using compost worms. As will be appreciated, the optimum proportions of the receptacle may vary somewhat dependent on the type and nature of the organic waste stream introduced to the receptacle 60 and the species of worms present within it.

The trapped castings and organic material then consolidate in the lower periphery 40 of the lower body 3 of the receptacle. Any worms present therein are encouraged to migrate upwards to the active surface layer due to the higher pressures in this lower periphery 40, and the lack of fresh food material.

In normal operation the processed organic waste is allowed to mature for a holding period, typically of several weeks, prior to removal from the farm. The holding period also allows any adult worms time to migrate upward towards the top of the receptacle 60 in search of fresh food material.

The design of the lower body 3 results in finished castings in only the lower periphery 40 of the outlet falling away from the farm when the outlet cover 4 is removed. In proper operation compression caused by the sloped walls 12 prevents castings from breaking away any higher than the end of the taper 10. This feature enables harvesting a specific volume of castings, in a compressed state, each time the outlet cover is removed.

The compressed processed material can be accessed when required from the lower periphery 40 of the lower body 3 of the receptacle 60 by releasing the catches 9 holding the outlet cover 4 in place and sliding said outlet cover 4 downwards away from the receptacle 60. Moreover, the volume of the outlet cover 4 is comparable to that of the lower periphery 40 of the lower body 3, thus the compressed material takes up the space in the outlet cover 4.

In a typical situation this will be as often as once per month. As will be appreciated, the way in which the outer cover 4 is releasably attached to the lower portion 3 of the receptacle 60 ensures minimal disturbance to life cycle of the worms.

Complete removal of the outlet cover 4 has the advantage of allowing the processed waste to be removed evenly and completely from the lower part 3 of the receptacle 60 in a compressed state. In a compressed state the processed organic material contains less water than in an uncompressed state and accordingly takes up less volume than uncompressed material, a benefit in both processing and handling.

Normal operation of the worm farm results in very little if any worms present in the lower portion 3 of the receptacle 60, significantly reducing the handling required in order to separate worms from processed waste once removed from the receptacle 60.

Following the removal of processed waste, the outlet cover 4 is reinstated over bottom portion 40 of the lower body 3 by sliding upwards over the bottom portion and secured using the catches 9 on each side.

If worms are present in the compressed material, the upper lid 1 of the receptacle 60 can be inverted, and the collected organic material placed directly upon it. Any worms present will move away from the surface of the organic material to escape the light, allowing the surface layer to be collected. After a subsequent period of time additional material can be removed from the surface as the worms present move away from the light. Once any worms present have been separated in this manner they can be returned to the top of the active layer in the receptacle 60, and the lid 1 re-instated in its normal operating position.

While the above example has been illustrated and described, it will be appreciated that various changes can be made therein without departing from the spirit and scope of the invention. For example, in the preferred embodiment, the passage of liquid is able to pass unrestricted from the receptacle. In optional embodiments the drain hole may be adapted with a tap or other suitable mechanism to enable liquid to be drained from the outlet cover 4 on demand. In such an alternative embodiment a ledge may be provided on the inner side walls of the outlet cover such that the filter 13 is supported at a suitable distance from the floor of the outlet cover 4.

As explained the invention produces compressed material which comprises castings and organic matter and being substantially devoid of worms. At least certain embodiments have advantages relative to existing apparatus, in that the compressed material has a lower water content, and significantly reduced worms in the finished castings. In addition the configuration of the apparatus of the invention is easier to handle, simpler to operate and minimises the disturbance of the worms lifecycle. Furthermore castings are cured within the receptacle before harvesting.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A vermicomposter apparatus to treat organic matter with worms, comprising:
a receptacle including:
side walls including:
an upper portion which is downwardly tapering and configured to facilitate compression of organic matter as said organic matter is processed,
a lower portion connected at a connecting line with a lower edge of said upper portion and which extends vertically without any taper,
an upper entry aperture defined by an upper periphery of the respective side walls and configured for loading said receptacle with organic matter and worms and
a lower discharge aperture configured to discharge compressed material comprising castings and organic matter, wherein the lower discharge aperture is defined by a lower periphery of the lower portion;
a base lid completely removably connected to the receptacle at the lower discharge aperture and adapted to releasably close said discharge aperture and configured to permit removal of said compressed material from said receptacle, the base lid including a bottom having:
a liquid drain opening, and a filter positioned at a lower portion of said base lid immediately above said liquid drain opening, for restricting the passage of compressed material; and a securing arrangement for releasably securing said base lid to said receptacle at said lower discharge opening to completely remove said lid from said receptacle;

a support for elevating said receptacle off a ground surface to a height such that the base lid is spaced from the ground surface so as to be completely removable from said receptacle, and the receptacle sits within the support such that the upper portion of the receptacle contacts the support; the support includes a frame and an element connected to the frame for elevating said frame above the ground surface;

the lower portion having a length which serves to hold compressed material to be removed and which is discharged into said base lid above said filter, while permitting removal of the compressed material in the lower portion below the connecting line when said base lid is completely removed from the receptacle.

2. The vermicomposter apparatus according to claim 1 wherein the receptacle has a central axis and the downwardly tapering side walls are angled at between 5and 20 degrees with respect to the central axis.

3. The vermicomposter apparatus according to claim 2 wherein the downwardly tapering side walls are angled at between 10 and 15 degrees with respect to the central axis.

4. The vermicomposter apparatus according to claim 1 wherein the lower periphery of said side walls are non-tapered.

5. The vermicomposter apparatus according to claim 4 wherein the base lid comprises a sleeve adapted to fit said lower periphery and to retain said compressed material after disengagement of said base lid from said receptacle.

6. The vermicomposter apparatus according to claim 5 wherein a height of said lower periphery is equal to a height of said sleeve.

7. The vermicomposter apparatus according to claim 1 wherein the upper periphery of said side walls are non-tapered.

8. The vermicomposter apparatus according to claim 1 wherein an interior surface of the receptacle is smooth to enhance the rate at which said organic matter is compressed as said organic matter is processed.

9. The vermicomposter apparatus according to claim 1 further comprising an entry lid adapted to engage said receptacle and releasably close said upper entry aperture.

10. The vermicomposter apparatus according to claim 9 wherein the entry lid comprises perforations adapted to allow the passage of gasses and liquids and to substantially prevent the entry of insects and exit of worms.

11. The vermicomposter apparatus according to claim 1 wherein the receptacle is manufactured from one of:
 a high density polyethylene,
 a plastic material and
 a plasticized material.

\* \* \* \* \*